United States Patent
Klardie et al.

(10) Patent No.: US 7,163,398 B2
(45) Date of Patent: *Jan. 16, 2007

(54) IMPRESSION CAP

(75) Inventors: Michael R. Klardie, Bloomington, MN (US); Robert D. Carter, Apply Valley, MN (US)

(73) Assignee: Lifecore Biomedical, Inc., Chaska, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/099,930

(22) Filed: Mar. 13, 2002

(65) Prior Publication Data

US 2003/0175655 A1  Sep. 18, 2003

(51) Int. Cl.
*A61C 8/00* (2006.01)
(52) U.S. Cl. .................................................. 433/173
(58) Field of Classification Search .............. 433/173, 433/172, 174, 175, 221
See application file for complete search history.

(56) References Cited

U.S. PATENT DOCUMENTS

| 5,458,488 | A | * | 10/1995 | Chalifoux | 433/173 |
| 5,540,876 | A | * | 7/1996 | Larson et al. | 264/479 |
| 5,681,167 | A | | 10/1997 | Lazarof | |
| 5,762,500 | A | | 6/1998 | Lazarof | |
| 5,934,906 | A | * | 8/1999 | Phimmasone | 433/172 |
| 6,068,478 | A | * | 5/2000 | Grande et al. | 433/172 |
| 6,142,782 | A | | 11/2000 | Lazarof | |
| 6,161,729 | A | * | 12/2000 | Gentile et al. | 222/94 |
| 6,561,805 | B1 | * | 5/2003 | Kumar | 433/174 |
| 6,672,871 | B1 | * | 1/2004 | Hurson | 433/172 |
| 2001/0034008 | A1 | | 10/2001 | Porter et al. | |
| 2002/0004189 | A1 | | 1/2002 | Hurson | |
| 2002/0106610 | A1 | | 8/2002 | Hurson | |
| 2003/0082499 | A1 | * | 5/2003 | Halldin et al | 433/173 |

FOREIGN PATENT DOCUMENTS

WO    WO 02/17814 A1    3/2002

* cited by examiner

*Primary Examiner*—Melba Bumgarner
(74) *Attorney, Agent, or Firm*—Dorsey & Whitney LLP

(57) ABSTRACT

An Implant/Abutment Impressioning cap. The impression cap is multi-vented and configured to uniquely fit over an abutment/implant assembly and grasp the implant via a novel flange and internal geometry design. The flange is located at the bottom of the impression cap forming a bottom rim and is constructed to grasp the collar of an implant in a press/friction fit manner. The internal geometry of the impression cap forms surfaces which mirror those of the abutment/implant assembly. The flange of the impression cap automatically captures the implant margin by pushing gingival tissue away when the component is seated.

41 Claims, 16 Drawing Sheets

FIG. 7

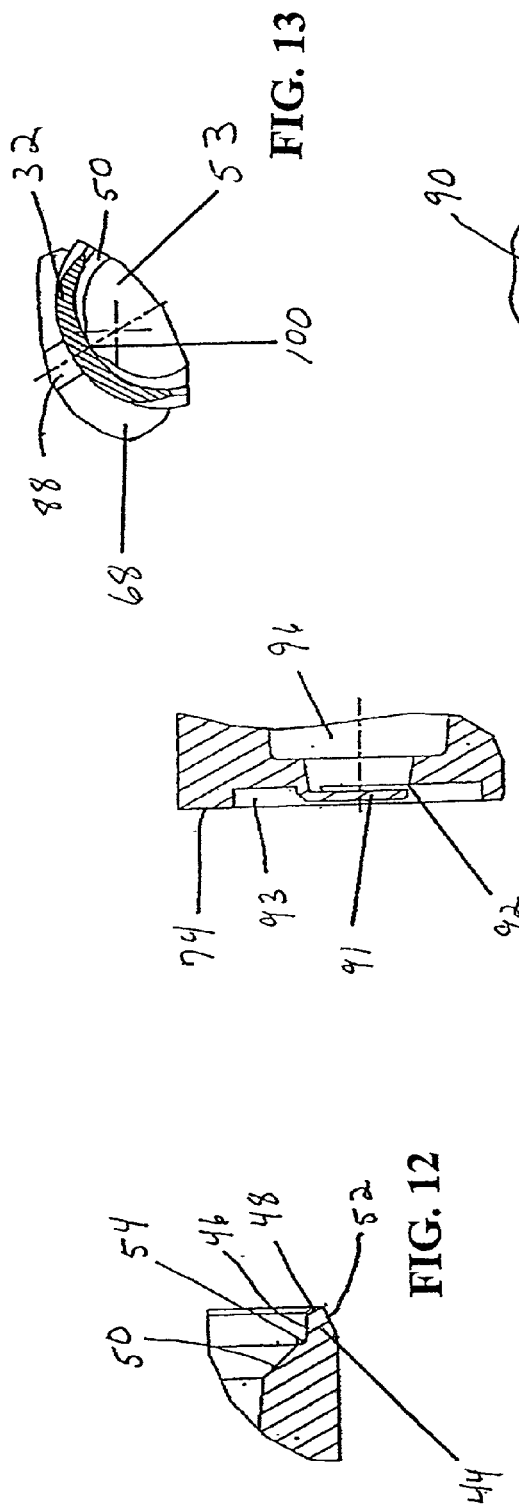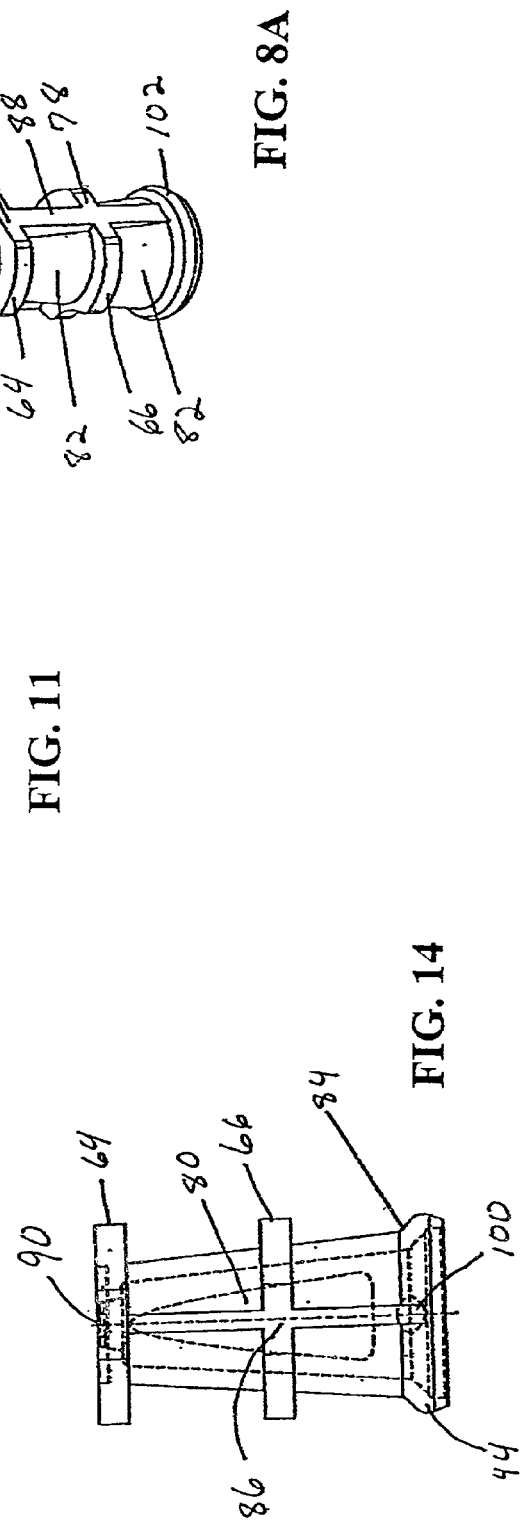

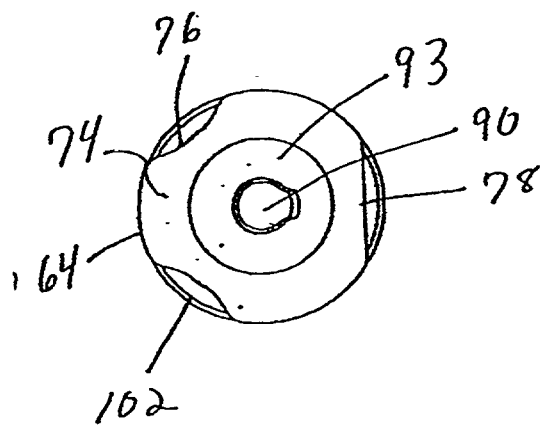
FIG. 16
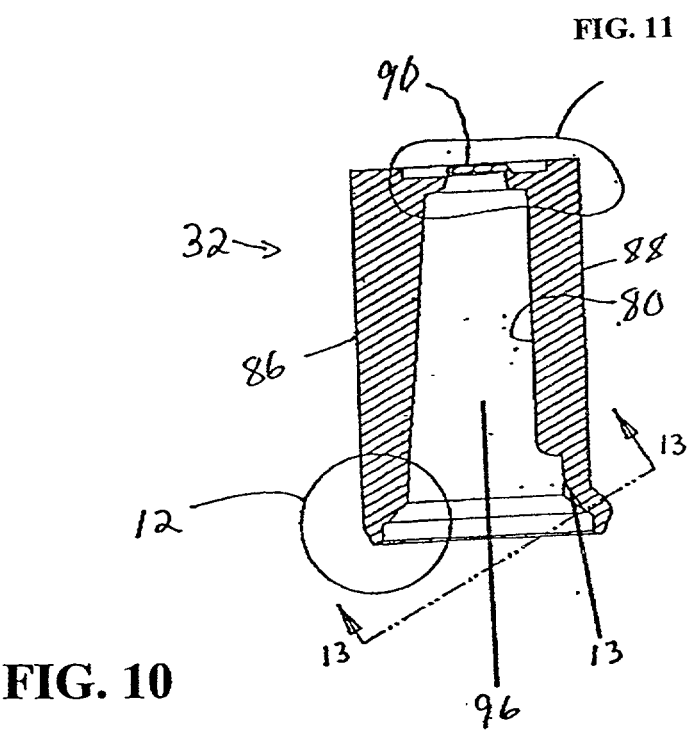
FIG. 10
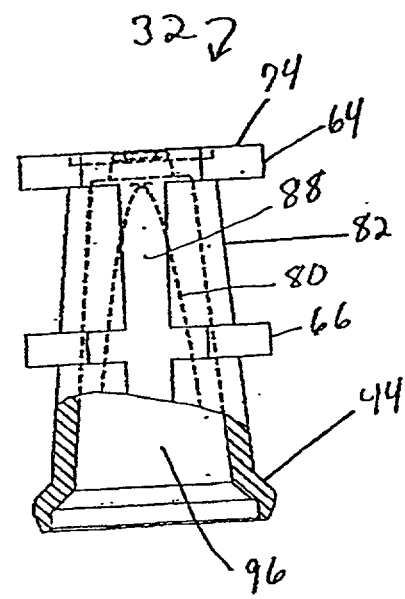
FIG. 11
FIG. 15
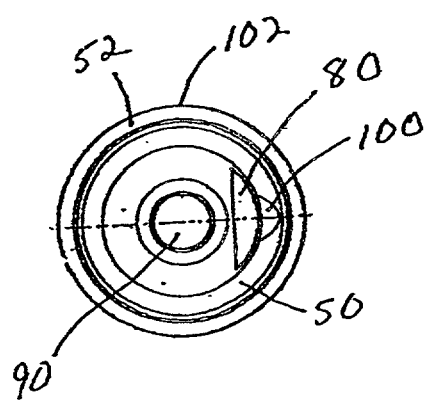
FIG. 17

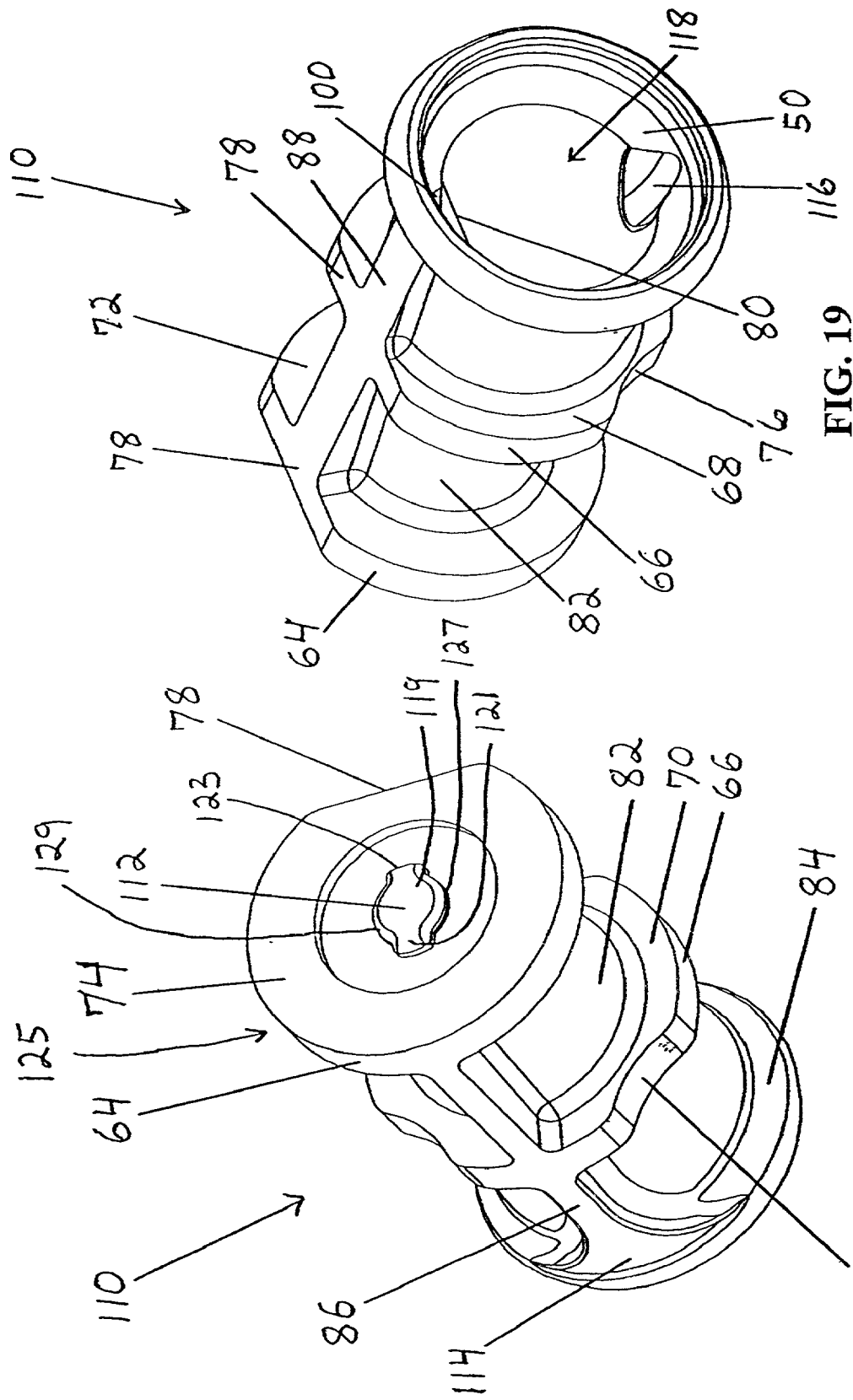

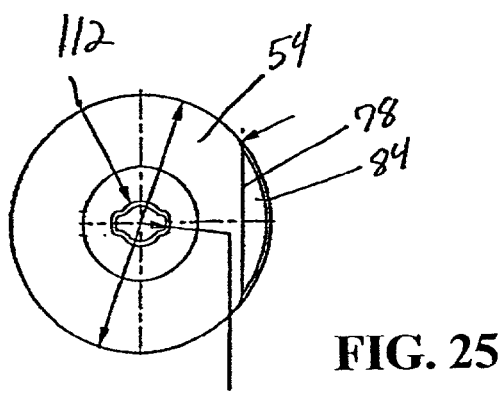
FIG. 25
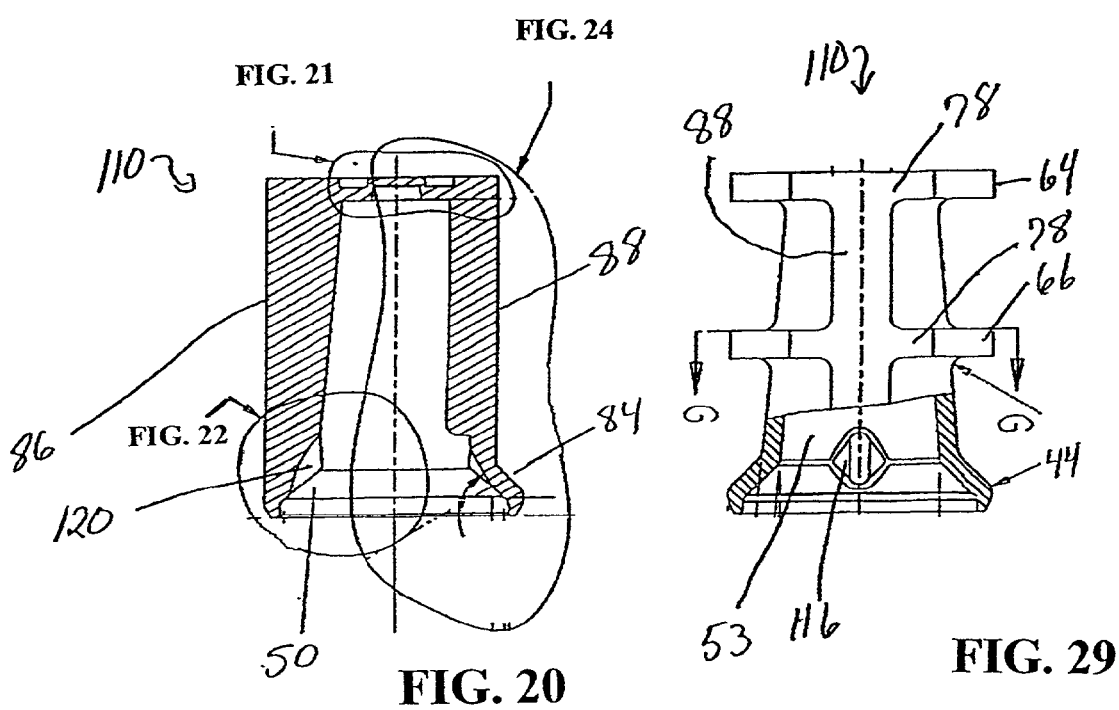
FIG. 20
FIG. 29
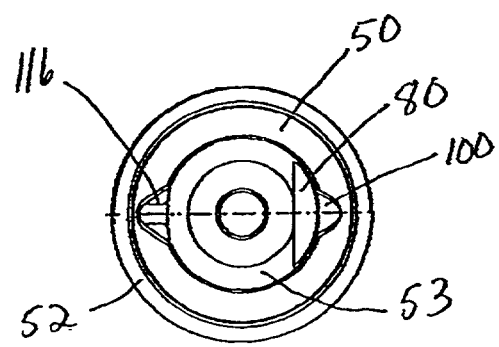
FIG. 26

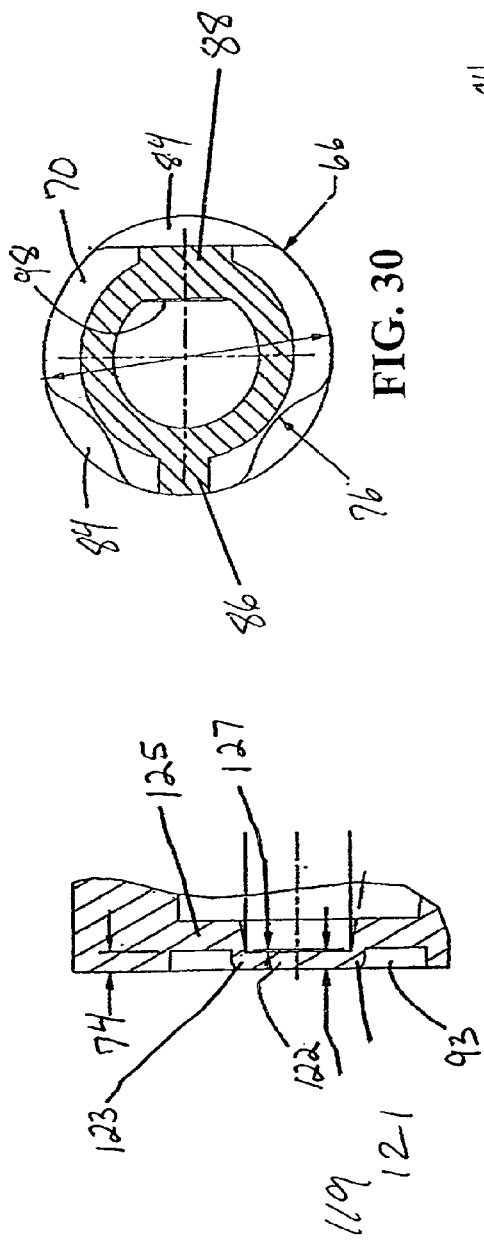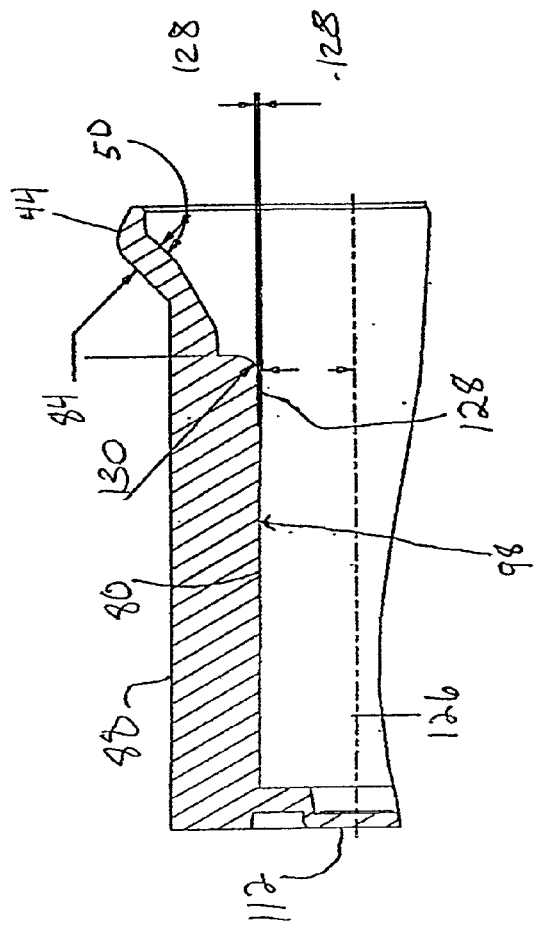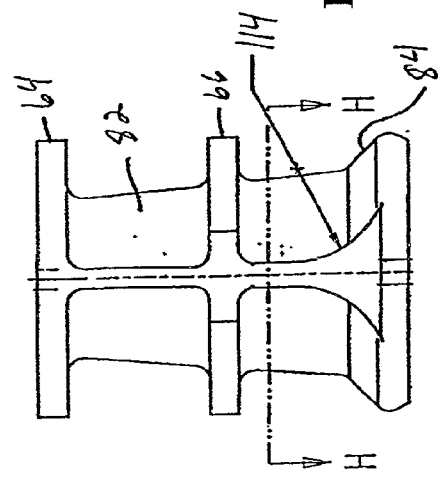

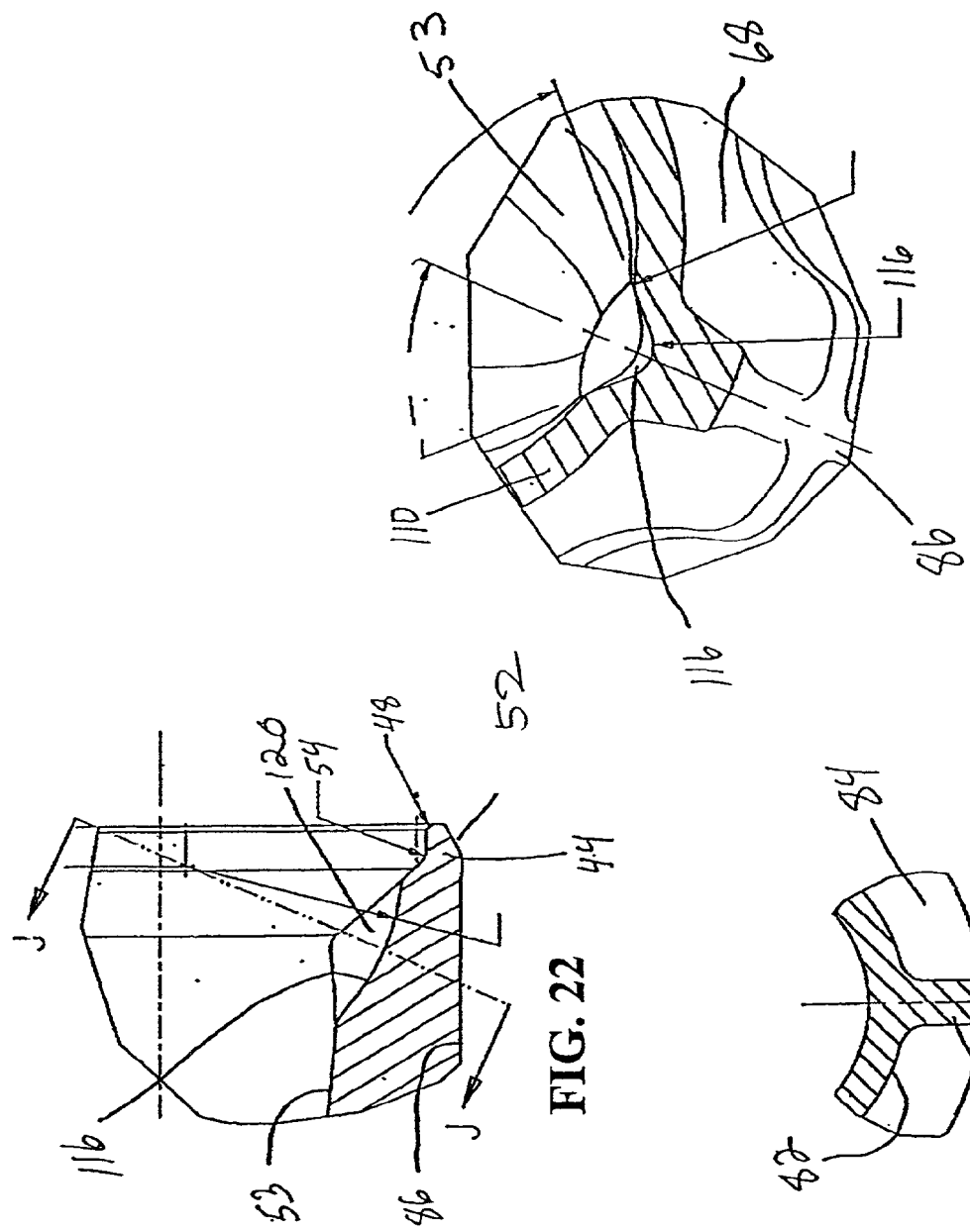

IMPRESSION CAP

FIELD OF THE INVENTION

The present invention relates to an Inplant/Abutment Impressioning System with a novel impression cap for an implant fitted in the human body in order to transfer the implant end protruding from the tissue structure to a master cast.

BACKGROUND

The following discussion refers in the first instance to the example of dental implants. For taking an impression of the situation in the patient's mouth and for transferring the impression obtained to a master cast, on which the tooth replacement is then modeled, a number of elements have hitherto been used. The work steps that have had to be performed, and the elements used in these work steps, are dealt with in detail by SCHROEDER, A.; SUTTER, F.; BUSER, D.; KREKELER, G.: Orale Implantologie [Oral implantology], Georg Thieme Verlag Stuttgart, 2nd edition, 1994, page 202 et seq. On the one hand, the assembling of the elements in the patient's mouth, particularly in the area of the molars, is problematic because of the resulting overall height of the elements, especially if a screwing instrument has to be used as well. Moreover, the work procedures are demanding for the patient, and they are time-consuming as regards impression-taking and production of the master cast. In addition to this, inaccuracies occur. The difficulties result primarily from the fact that the impression cap does not hold itself on the implant fitted in the mouth or on the manipulation implant to be used subsequently in the production of the master cast. DE 44 15 670 A1 discloses an impression cap which, at the open end facing the implant, has resilient flaps which, when applied, engage over the shoulder of the conical superstructure, the latter being fitted into the implant. The impression cap described there cannot therefore be used for taking an impression of the implant end protruding from the gingiva and projecting into the mouth, but instead only for taking an impression of the outer contour of the superstructure while the implant is positioned below the gingiva.

U.S. Pat. No. 6,068,478 discloses alternatives to the prior impression/implant systems. U.S. Pat. No. 6,068,478 describes an impression system which comprises as its principal component an impression cap for transferring an end, protruding from a human tissue structure, of an implant which is fitted in the human body, including possible superstructures, to a master cast. The outwardly directed implant end has an undercut contour on its outside, and the impression cap has a geometry which complements the undercut contour and engages therein. The undercut contour is formed either by an implant geometry tapering in a trumpet shape towards the implant bed, or by a recess near the implant end. After the impression cap is secured to the implant, it is encased in impression material. The impression cap embedded in the impression compound present in the impression tray is removed from the fitted implant and receives a manipulation implant to make a master cast.

The present invention addresses further constructive alternatives to the prior impression/implant systems.

All U.S. patents and applications all other published documents mentioned anywhere in this application are incorporated herein by reference in their entirety.

Without limiting the scope of the invention in any way, the invention is briefly summarized in some of its aspects below.

SUMMARY

The present invention is an Implant/Abutment Impressioning System for taking impressions of Cement-on-Crown abutments to mirror the contour of the soft tissue and bone as accurately as possible. More particularly, the invention discloses a novel impression cap. The impression cap is configured to uniquely fit over an abutment/implant assembly and grasp the implant via a novel flange and internal geometry design. The flange is located at the bottom of the impression cap forming a bottom rim and is constructed to grasp the collar of an implant in a press/friction fit manner. The internal geometry of the impression cap forms surfaces which mirror those of the abutment/implant assembly. The flange of the impression cap automatically captures the implant margin by pushing gingival tissue away when the component is seated. This eliminates the need to pack cord, a common but tedious dental procedure.

An embodiment of the invention also includes a one way air vent positioned on the top of the impression cap. The one-way pressure releasing vent allows air to be released from the internal cavity, but seals to prevent external material from entering the internal impression cap cavity.

A secondary vent may also be formed in the impression cap, positioned in the inner surface of the lower rim of the impression cap. The secondary vent functions as a relief passage from the internal cavity to the outside. The relief passage vents the internal air pressure during assembly of the impression cap to the abutment/implant.

In a particular embodiment, the impression cap also has contoured retention geometry. The geometry, which is discussed in detail below, comprises a plurality of ribs, both circumferential and vertical. These ribs provide protrusions and additional surfaces for added retention between the impression material and the impression cap. The particular geometry used also functions as an external abutment feature during the impressing procedure. Thus, enabling proper positioning of an abutment analog to reproduce the abutment orientation and implant position.

The invention also contemplates sterilizing the impression cap via gamma sterilization. For this, a material must be chosen which is gamma sterilizable. Suitably a gamma sterilizable plastic, or more suitably a gamma sterilizable polypropylene, may be used.

BRIEF DESCRIPTION OF THE ATTACHED DRAWINGS

FIG. 8A is a perspective view of an impression cap;

FIG. 10 is a cut-away view showing a partial cross-section of the impression cap;

FIG. 11 is a detailed cut-away view showing a partial cross-section of a portion of FIG. 10, as indicated;

FIG. 12 is a detailed cut-away view showing a partial cross-section of a portion of FIG. 10, as indicated;

FIG. 13 is a detailed cut-away view showing a partial cross-section along lines 13—13 of FIG. 10;

FIG. 14 is side view of the impression cap with phantom lines;

FIG. 15 is a partial cross-sectional view of the impression cap with phantom lines;

FIG. 16 is a top view of the impression cap;

FIG. 17 is a bottom view of the impression cap;

FIG. 18 is a perspective view of an alternative embodiment of the impression cap;

FIG. 19 is a perspective view of the alternative embodiment of the impression cap;

FIG. 20 is a cut-away view showing a partial cross-section of the alternative embodiment of the impression cap;

FIG. 21 is a detailed cut-away view showing a partial cross-section of a portion of FIG. 20, as indicated;

FIG. 22 is a detailed cut-away view showing a partial cross-section of a portion of FIG. 20, as indicated;

FIG. 23 is a detailed cut-away view showing a partial cross-section along lines J—J of FIG. 22;

FIG. 24 is a detailed cut-away view showing a partial cross-section of a portion of FIG. 20, as indicated;

FIG. 25 is a top view of the alternative embodiment of the impression cap;

FIG. 26 is a bottom view of the alternative embodiment of the impression cap;

FIG. 27 is side view of the alternative embodiment of the impression cap shown in FIG. 25;

FIG. 28 is a detailed cut-away view showing a partial cross-section along lines H—H of FIG. 27;

FIG. 29 is a partial cross-sectional view of the alternative embodiment of the impression cap;

FIG. 30 is a detailed cut-away view showing a partial cross-section along lines G—G of FIG. 29;

DETAILED DESCRIPTION OF THE EMBODIMENT

Figure 1:
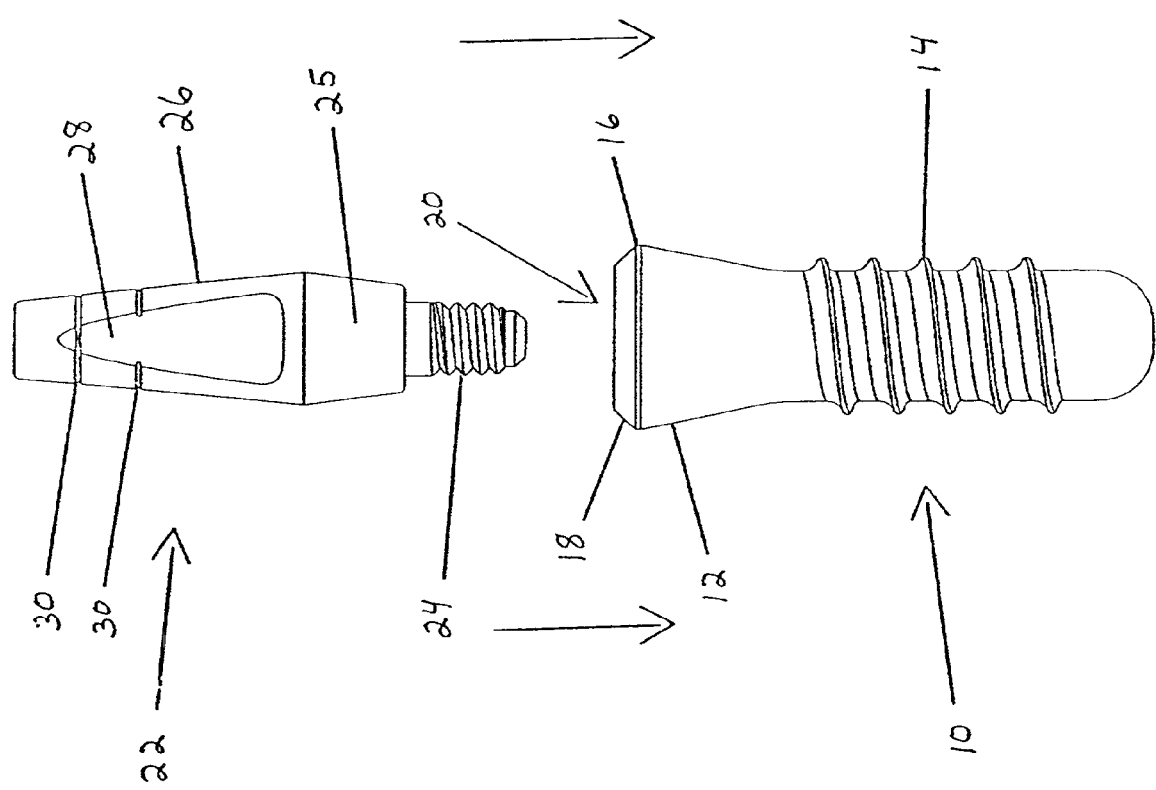
FIG. 1 is an implant and an abutment piece in an exploded view.

A detailed description of illustrative embodiments of the impression system according to the invention is given herein below with reference to the attached drawings, and possible modifications are discussed by way of conclusion.

The following statement applies to the whole of the description. If, for the purposes of clarity of the drawings, reference numbers are included in a figure but are not mentioned in the directly associated text of the description, then reference is made to their mention in preceding figure descriptions. In the interests of intelligibility, the repeated designation of components in succeeding figures is for the most part omitted, if it is clear from the drawings that the components concerned are "recurring" components.

Due to the multiple novel features disclosed herein, it should be understood that individual features of the embodiments may stand alone as improvement or may be combined with each other in multiple configurations where physically possible. The proportional representation illustrated by the figures also represents structural disclosure of various embodiments.

Elements not identified in a particular figure are readily identifiably via their identification in other figures.

Without wishing to limit the invention thereto, the example further refers to the taking of an impression of an implant 10 fitted in the mouth of a patient, here a dental implant as a full screw. The implant 10 has an implant head 12 widening conically upwards and threads 14 for insertion into the patient. The implant head 12, which will be shown in detail in later figures, forms an implant collar 16 and an angled implant surface or shoulder 18. An internal threaded bore 20 is also formed in the implant 10.

An abutment piece 22 is screwed into the implant 10 via its threaded part 24 into the internal threaded bore 20 of the implant 10. The abutment piece 22 has a base 25 an abutment 26, which is generally conical and has a female abutment flat 28. The abutment 26 may have one or more abutment flats 28. An abutment flat 28 is a generally vertically extending groove used to prevent rotation when further pieces are placed over the abutment 26.

The abutment 26 also has one or more circumferential grooves 30. The grooves provide additional retention of the crown after cementing. They also may be used to indicate the height of the abutment so that the user may determine the appropriate cap. Typical heights include 4.0 mm and 5.5 mm.

Figure 2:
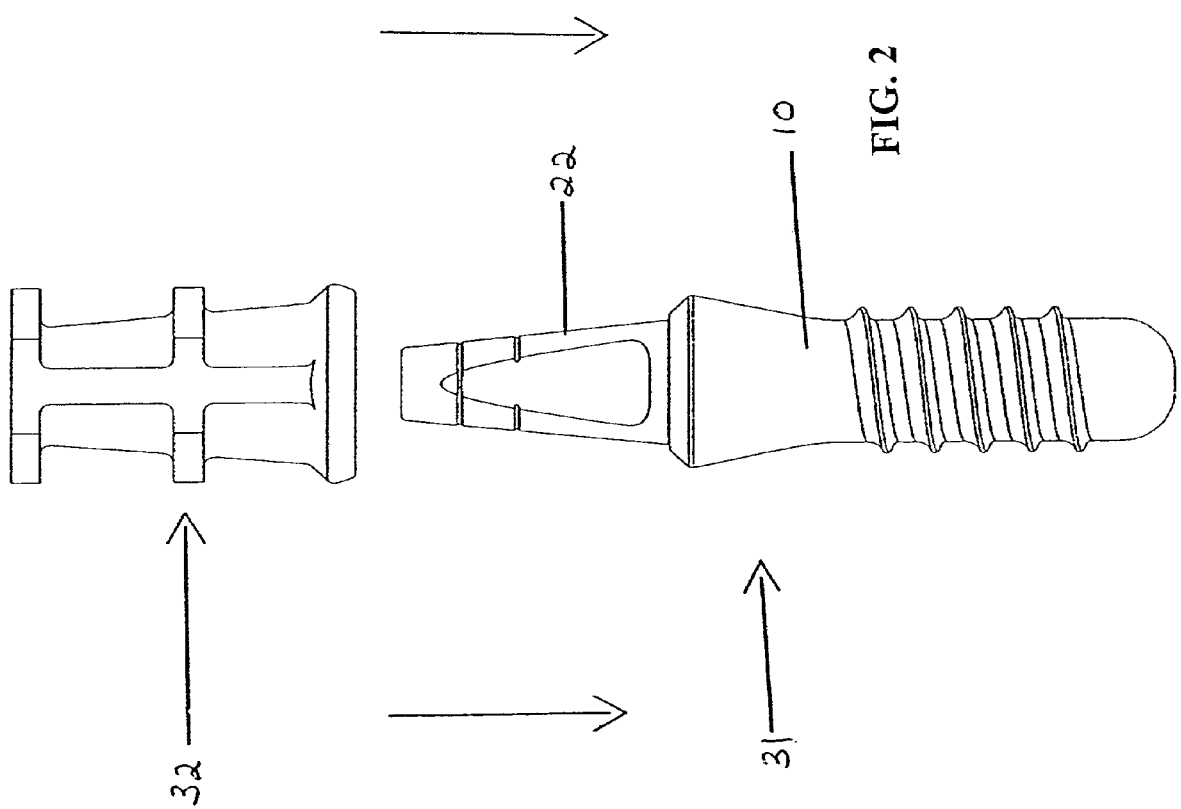
FIG. 2 is an implant/abutment assembly and an impression cap in an exploded view.
Figure 3:
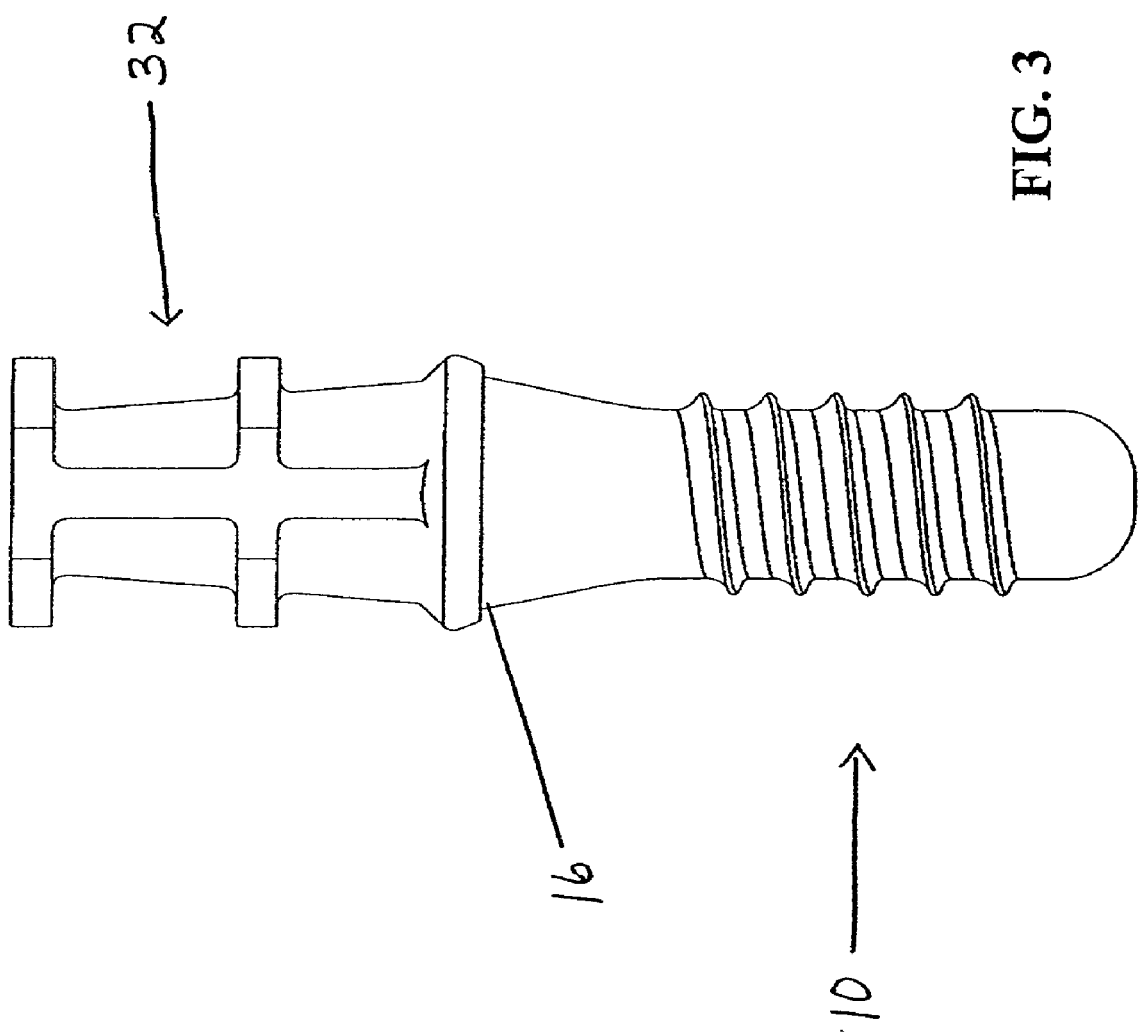
FIG. 3 is an implant/abutment assembly and an impression cap mounted thereon.

FIG. 2 shows the abutment piece 22 screwed into the implant 10. An impression cap 32 is then lowered over the abutment 26. As will be shown below, the internal geometry of the impression cap 32 is configured to uniformly fit over the abutment 26. FIG. 3 illustrates the impression cap 32 lowered onto the abutment piece 22.

In FIG. 3, the impression cap 32 press fits down over the collar 16 of the implant 10 to capture the implant margin and position. Impression material is then placed over and around the impression cap 32 to take an impression of the gum around the abutment/implant assembly. The impression material is then removed from the abutment 26 and the patient. The impression cap 32 remains is the impression material when it is removed.

Figure 4:
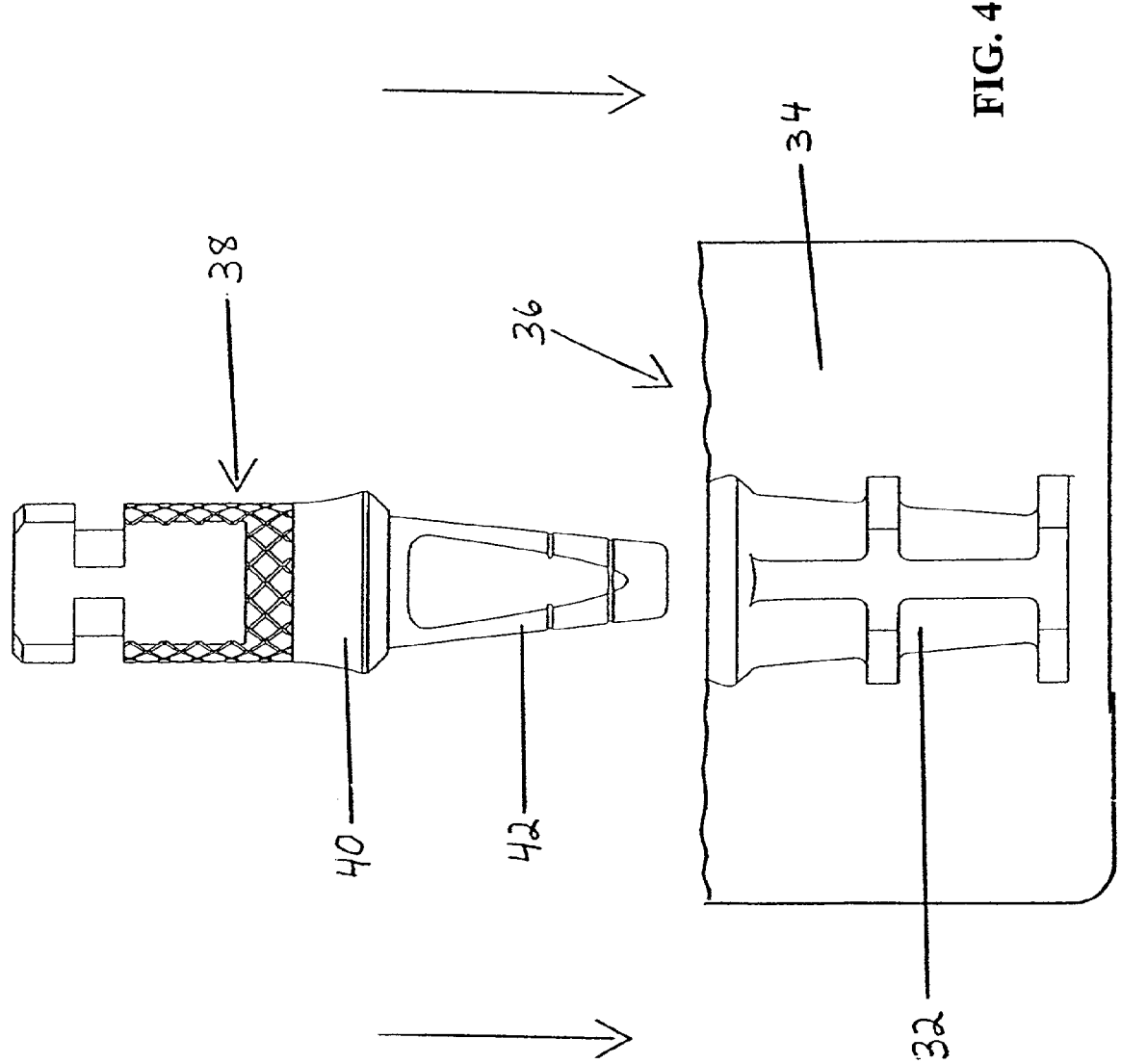
FIG. 4 is an abutment piece in an impression material tray and an analog in an exploded view.

FIG. 4 shows the removed impression cap 32 in the impression material 34. A negative 36 of the gum surface is formed in the impression material 34. An analog 38 is then inserted into the impression cap 32. The analog 38 has a handle 39, a head 40 and an abutment 42 which mimic the shape of the abutment 26 and head 12 of the abutment/implant assembly 31. This provides for a fit which replicates the fit between the impression cap 32 and the abutment/implant assembly 31.

Figure 5:
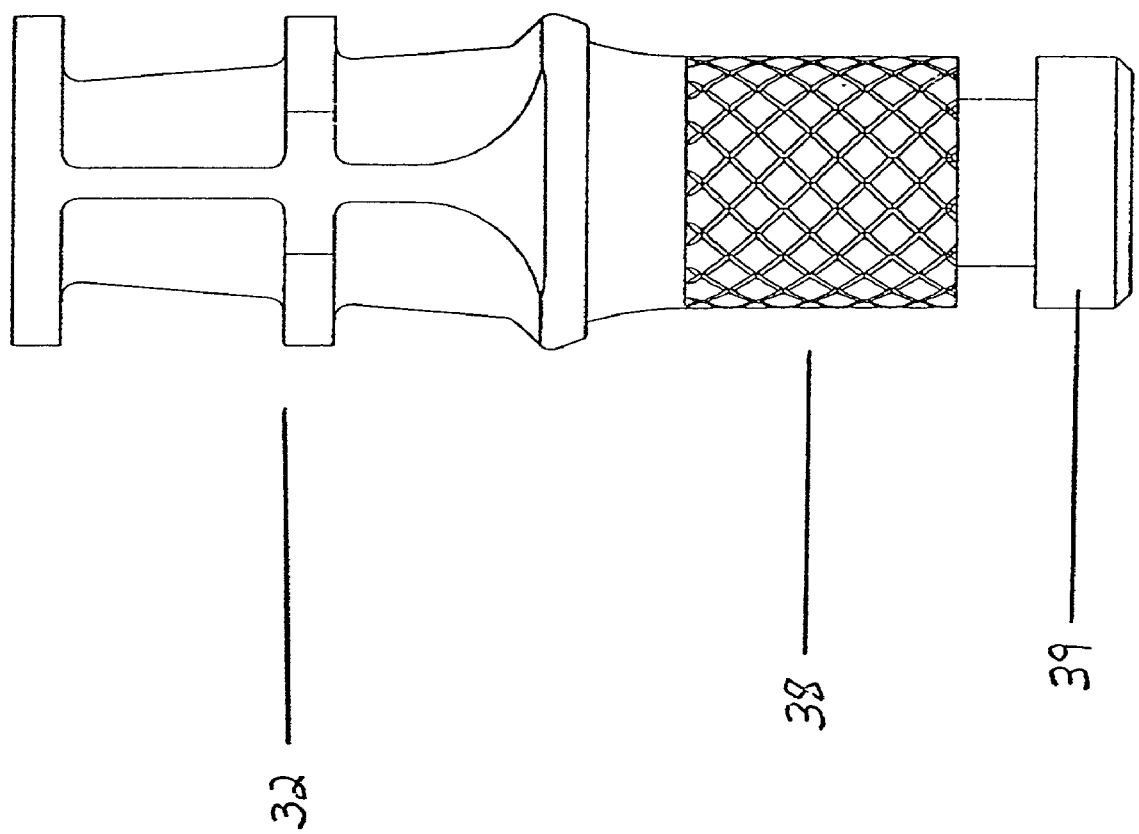
FIG. 5 is an abutment piece in an impression material tray and an analog in an assembled view.

FIG. 5 shows the engagement between the impression cap 32 within the impression material (not shown) and the analog 38. A stone model is then poured over and around the analog 38 and onto the surface of the impression material 36. After the stone model sufficiently hardens, the impression cap 32 and the impression material 36 are removed leaving the analog 38 and the newly formed stone model, wherein the stone model has a surface which mimics the surface of the gum line around the inserted abutment/implant assembly 31. The analog 38 remains fixed in the stone model and together they replicate the position of the Cement-on-Crown Abutment that is in the patient's mouth. This apparatus may be used for future construction of dental implants which will fit uniformly in the patient's mouth.

Further discussion will address particular components of the Inplant/Abutment Impressioning System.

Figure 6:
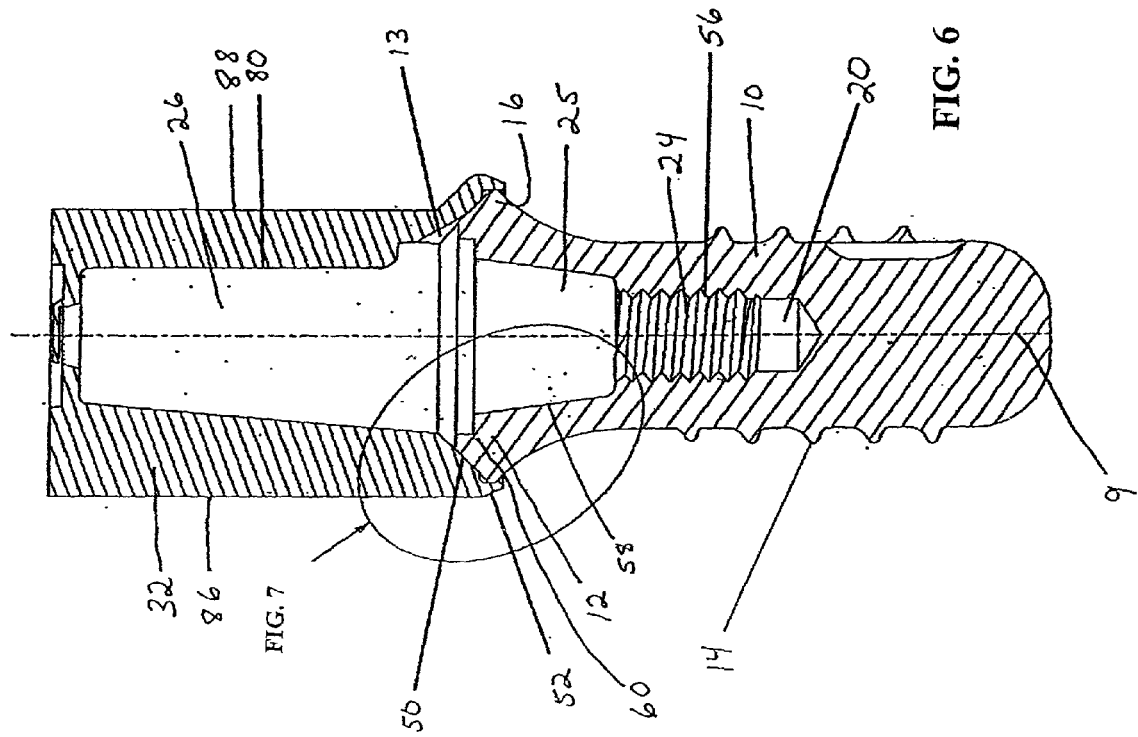
FIG. 6 is a cut-away view showing a partial cross-section of an implant/abutment assembly and an impression cap mounted thereon.
Figure 7:
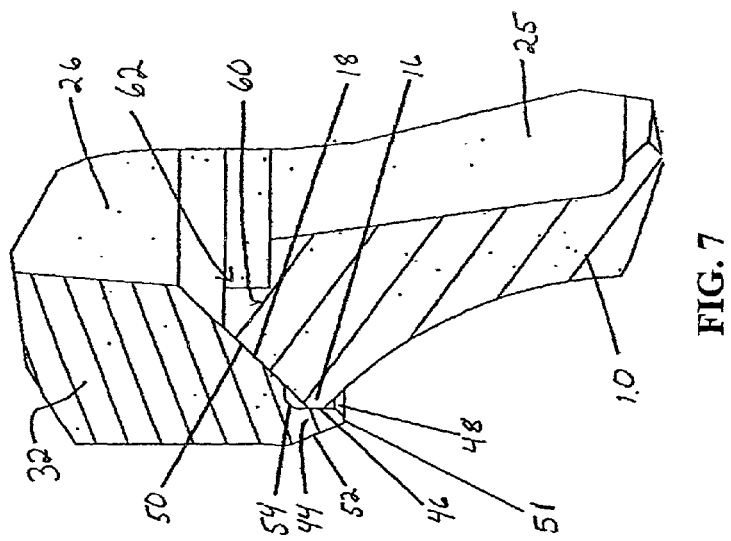
FIG. 7 is a detailed cut-away view showing a partial cross-section of a portion of FIG. 6, as indicated.

FIG. 6 illustrates a cross-sectional view of FIG. 3. The device is positioned to view the abutment flat 28 from the side. In this figure, the impression cap 32 is snuggly positioned on the abutment 26, which is screwed into the implant 10. FIGS. 6 and 7 are being used partly to illustrate the fit between the impression cap 32 and the abutment/implant assembly 31, as well as the fit between the abutment piece 22 and the implant 10.

FIG. 7 is a blown-up view of a portion of FIG. 6, as indicated in FIG. 6. Except for a secondary vent 13, which will be discussed below, FIG. 7 illustrates the engagement between the press fit mechanism of the impression cap 32 and the implant 10. This engagement occurs primarily between the peripheral portions of the collar 16 of the implant 10 and the engagement end or press fit mechanism of the impression cap 32. The press fit or friction fit of the impression cap is produced by the press fit mechanism of the cap. The mechanism provides an inwardly directed radial force against the periphery of the collar.

As shown in FIG. 7, at the engagement end, the press fit mechanism of the impression cap 32 has a circumferential flange 44 to guide the engagement end of the impression cap 32 over the collar 16 of the implant 10. The flange 44 has a press or squeeze surface 46 which is substantially parallel with the axis 9 of the implant 10 and press fits to the maximum diameter of implant collar 16. The connection between the flange 44 and the collar 16 is a pressure frictional fit, wherein the flange 44 squeezes the outer surface of the collar 16. The outer surface of the collar 16 which contacts the flange 44 may be flat to provide a greater contact surface.

The flange 44 further includes a lead in taper 48 to guide the flange 44 over the collar 16. During assembly of impression cap 32 onto implant 10, taper 48 contacts the outer surface of the implant collar 16 first. The taper 48 helps expand the impression cap 32 so that pressing surface 46 can press fit (or friction fit) to the maximum diameter of implant collar 16. The lead in taper 48 can be a chamfer, radius, or the like.

The impression cap 32 also comprises an angled surface 50 which provides a reference stop with the shoulder 18 of the implant 10. This surface 50 to surface 18 contact provides a consistently accurate means of determining that the impression cap 32 is fully seated on the implant/abutment assembly 31. The impression cap 32 angled surface 50 mates with the angled implant surface, or shoulder 18. When the impression cap angle surface 50 contacts the implant shoulder 18, it produces a tactile feel, which indicates to the user that the impression cap 32 is fully seated. When the impression cap 32 and implant 10 are fully seated, the angled surfaces (50 & 18), provides stability by aligning and self-centering the impression cap 32 on the implant 10.

The flange 44 further includes angled surface 52 formed by its exterior. This surface 52 retracts the gingival tissue away from the implant table. This allows the impression cap 32 to automatically capture the implant margin, or collar 16. This also eliminates the need to pack cord, a common but tedious dental procedure.

The engagement end of the impression cap 32 also forms a curved relief 54 between angled surface 50 and the body of the flange 44. This relief 54 removes the acute angle formed between the pressing surface 46 and the angled or stop surface 50. The curved relief 54 removes any stress risers that may occur within the material during assembly as the lead in taper 48 moves over the implant collar.

FIG. 7 further shows the fit between the abutment piece 22 and the implant 10. The implant 10 has a bored hole 20, which is partially threaded 56, partially conical 58 and partially stepped 60. These portions are mirrored by portions 24, 25 and 62 of the abutment piece 22 for a secure fit. The specific mirroring configurations are not critical as long as there is a snug fit between the implant 10 and the abutment piece 22.

Figure 8:
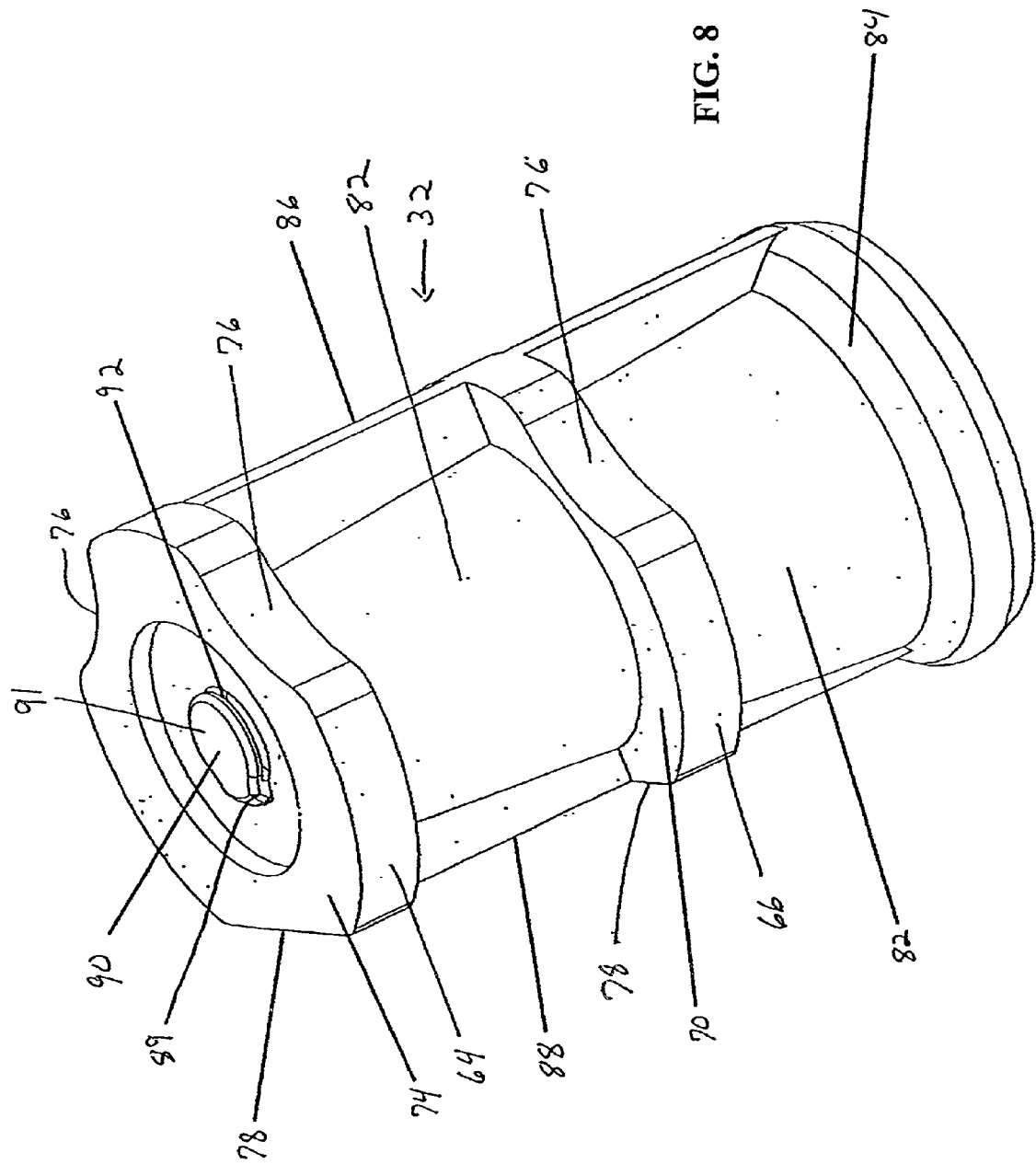
FIG. 8 is a perspective view of an impression cap.

FIG. 8 is a view of the outside of the impression cap 32. The outside of the impression cap 32 has contoured retention geometry (CRG). This CRG provides tension and compression resistance when the cap 32 is encased in impression material. The CRG comprises circumferential retention ribs 64 & 66 located at the top 64 and midway down 66 the exterior of the impression cap 32. Surfaces 68, 70, 72, & 74 (68 and 72 shown in FIG. 9) provide further tension and compression resistance when the cap 32 is encased in impression material.

The retention geometry also comprises one or more concave surfaces 76 to provide anti-rotation while encased within the impression material. The embodiment shown in FIG. 8 illustrates the concave surfaces 76 as being formed in the circumferential retention ribs 64, 66.

Anti-rotation is further provided by one or more flat surfaces 78, which are formed in retention ribs 64 and 66. Flat surfaces 78 within the retention geometry are aligned with internal flat 80 (shown in FIG. 9). This allows the flat surfaces 78 to be an indicator of the internal flat's 80 location. The flat surfaces can better be seen in FIG. 8A.

Generally, the impression cap 32 has a tapered body 82. The tapered body 82 allows surface area 72 on the upper retention rib 64 to be greater than the surface area 70 on the lower retention rib 66. It also allows the surface area 70 on the top of retention rib 66 to be greater than the surface area 68 on the bottom of retention rib 66. The increased surface area on the retention ribs 64, 66 allows for increased retention of impression cap 32 while encased within the impression material.

The tapered body 82 allows an increased amount of impression material to reside between the upper and lower retention ribs 64, 66 and between the lower retention rib 66 and angled surface 84. The increased impression material allows for increased retention of the impression cap 32 while encased within the impression material.

The impression cap 32 further comprises two vertical ribs 86, 88. Suitably these vertical ribs are located 180 degrees apart, relative to a center line through the cap 32 from the top to bottom. Vertical ribs 86 and 88 aid in strengthening the impression cap structure so that the impression cap 32 is not deformed from the compressive force imparted on it during seating of the impression cap 32 on the abutment/implant 31.

Vertical ribs 86, 88 also provide resistance to rotational movement of the impression cap 32 while encased within the impression material. In this embodiment, the vertical rib 86 has a greater horizontal depth than vertical rib 88 due to the presence of the flat surfaces 78. Both ribs 86, 88, have increasing horizontal depth from bottom to top for structural stability and for greater contact with the impression material. Vertical rib 88 extends downward from the center of the flat surface 78 and perpendicular to internal flat 80. This allows the vertical rib 88 to be an indicator of the internal flat's 80 location.

The impression cap 32 further comprises a one way vent 90 having a gap 92 for release of air during assembly. During the impressioning process when the impression material covers the cap, the impression material pushes against the vent 90 and seals gap 92. The seal does not allow impression material to enter the internal cavity 96 and no longer allows air to release.

Figure 9:
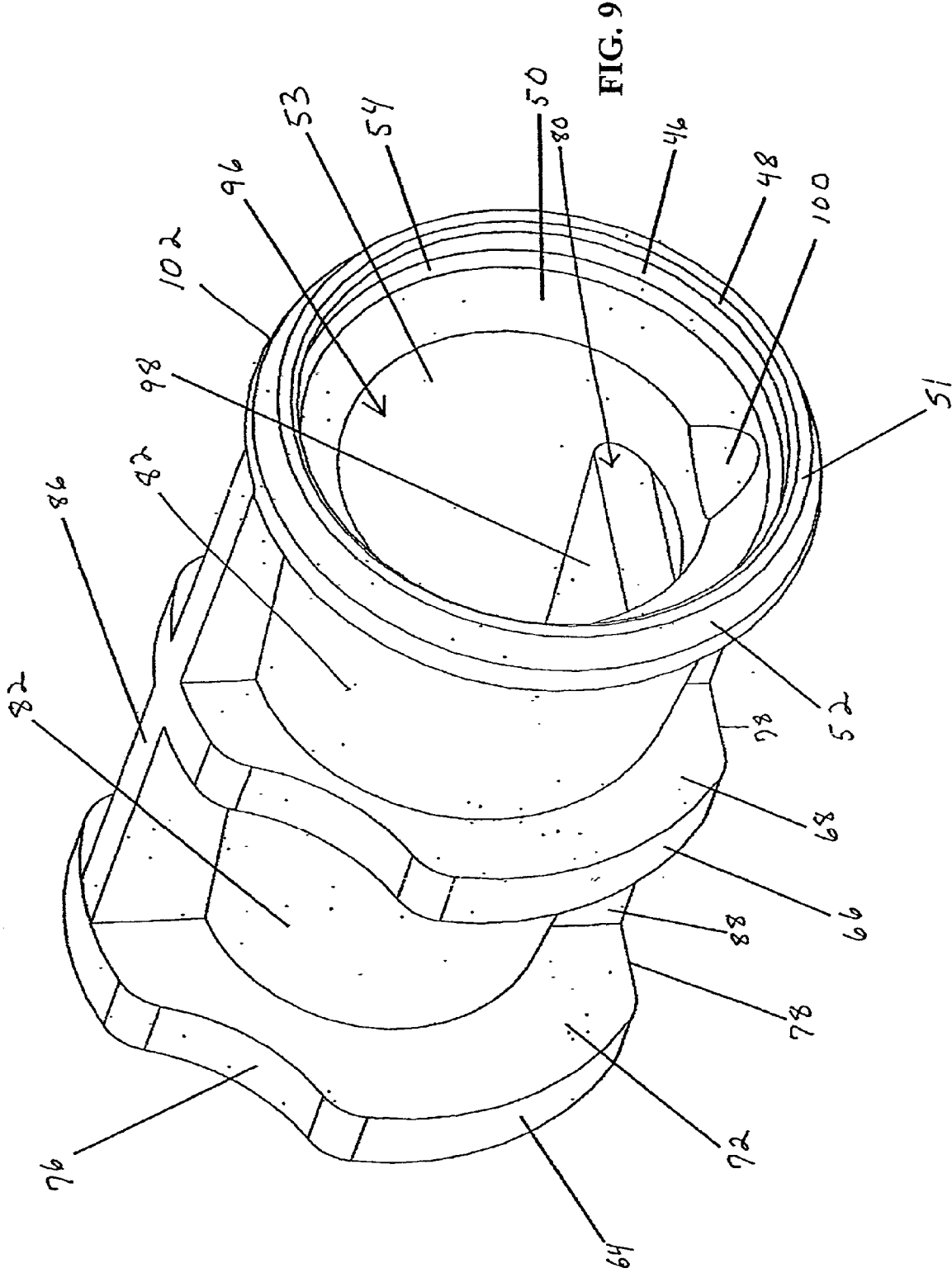
FIG. 9 is a perspective view of an impression cap.

FIG. 9 illustrates a view of the impression cap 32 from a further angle showing a portion of the internal geometry of the inner cavity 96. The internal geometry of the impression cap 32 matches the geometry of the abutment/implant connection 31. Internal or abutment flat 80, which has an inner surface 98, interrupts the inner surface 53 of the cap. The abutment flat 80 provides anti-rotation and rotational stability.

The impression cap 32 further comprises a channel 100 which forms the secondary vent 13 when the cap 32 is coupled with the abutment/implant assembly 31. While assembling the impression cap 32 to the abutment/implant 31, air compresses within the internal cavity 96 of the impression cap. The compressed air pushes against the impression cap 32 and causes the impression cap 32 to lift off the abutment/implant 31. Air pressure relief (release) is beneficial to alleviating the internal air pressure.

The secondary vent 13 is a relief passage from the internal cavity 96 to the outside. The secondary vent 13 is a relief passage in the reference stop surface 50. This allows the majority of the trapped air to escape during assembly of the impression cap 32 to the abutment/implant configuration 31.

Although only one channel 100 is shown, it should be understood that the invention contemplates a plurality of channels arranged around the angled surface 50. For example, an embodiment may have a channel 100 as shown in FIG. 9 and a second channel situated 180 degrees around the angled surface and aligned with rib 86.

FIG. 9 also illustrates the bottom rim 102 showing the surfaces which form the flange 44 of the cap 32. The curved relief 54 follows the angle surface 50 from the inside of the cap 32 toward the outside. The pressing surface is shown at 46, followed by the lead in taper 48. Angled surface 52 represents the outer part of the flange 44. The flange 44 may have an extra surface 51 between angled surface 52 and surface 48 to provide a blunt end to the flange 44. Surface 51 may be substantially perpendicular to pressing surface 46 or rounded.

FIG. 10 shows a cross-sectional view of the cap 32, wherein the internal flat 80 faces to the left. This figure provides a view of the geometry of the internal cavity 96. The positioning of the one way vent 90 and the secondary vent 13 are also shown.

Certain portions, which are indicated in FIG. 10, are blown up and can be seen in FIGS. 11–13. FIG. 11 illustrates the one way vent 90 at the top of the cap 32 in a cross-sectional view. The vent 90 comprises a cover 91 attached to the top of the cap 32 via an attachment piece 89 and a gap 92 to release the air, as described above. It is the cover 91 which is pushed down by the impression material to seal the gap 92. A recess 93 may also be formed to keep the top surface of the cover 91 at, or below, surface 74.

FIG. 12 shows a cross-sectional view of the flange 44 portion of the cap 32. The portions numerically indicated are described above. FIG. 13 shows a cross-sectional view along the line 13—13 shown in FIG. 10. Similarly, the portions numerically indicated are described above. In this figure, a cross-section of the cap material 32 is shown FIGS. 14–17 show the cap 32 from different angles. The portions numerically indicated are described above. FIG. 14 is a view of the cap 32, wherein the vertical rib 86 is centered in the front. The inner rear surfaces are shown in phantom. FIG. 15 is a view of the cap 32, wherein the vertical rib 88 is centered in the front. The figure is a partial cross-sectional view and the remaining inner rear surfaces are shown in phantom. FIG. 16 is a top view of the cap 32 and FIG. 17 is a bottom view of the cap 32.

FIG. 18–19 show a further embodiment, identified as 110, of the impression cap. Cap 110 is similar to cap 32, but it has certain differences which may be added individually. As such, similar features are labeled similarly. Starting at the top of the cap 110, as shown in FIG. 18, the circumferential retention rib 64 has a flat indicator surface 78, but is free of recesses, as shown in FIG. 8 at 76. However, this embodiment does have recesses 76 in circumferential retention rib 66.

A further embodiment of the top vent 112 is also shown. This vent 112 will be shown and described in more detail in reference to later figures.

Also shown in FIG. 18 is a further alternative in the construction of vertical rib 86. In this embodiment, the bottom end 114 of rib 86 is flared. This extra mass in the bottom 114 of rib 86 aids in preventing cracking during the manufacturing of the cap. In this embodiment, the extra mass is positioned adjacent a second secondary vent, which is formed by a second channel 116. Second channel 116 is formed similarly to channel 100 and is used similarly for venting. The extra mass provided by bottom end 114 replaces the mass lost in forming channel 116. Although bottom end 114 is shown in a flared configuration, the present invention contemplates other configurations to increase the mass of rib 86 at the bottom, adjacent to the second channel 116.

FIG. 19 illustrates a view of the impression cap 110 from a further angle showing a portion of the internal geometry of the inner cavity 118. As with cap 32, the internal geometry of the impression cap 110 matches the geometry of the abutment/implant connection 31. In this figure, channel 116, which forms a second secondary vent 120 when the cap 110 is coupled with the abutment/implant assembly 31, can be seen. Secondary vents 13 and 120 are formed and work similarly.

FIG. 20 shows a cross-sectional view of the cap 110, wherein the internal flat 80 faces to the left. This figure provides a view of the geometry of the internal cavity 96. The positioning of the one way vent 112 and the secondary vents 13, 120, are also shown.

Figure 24A:
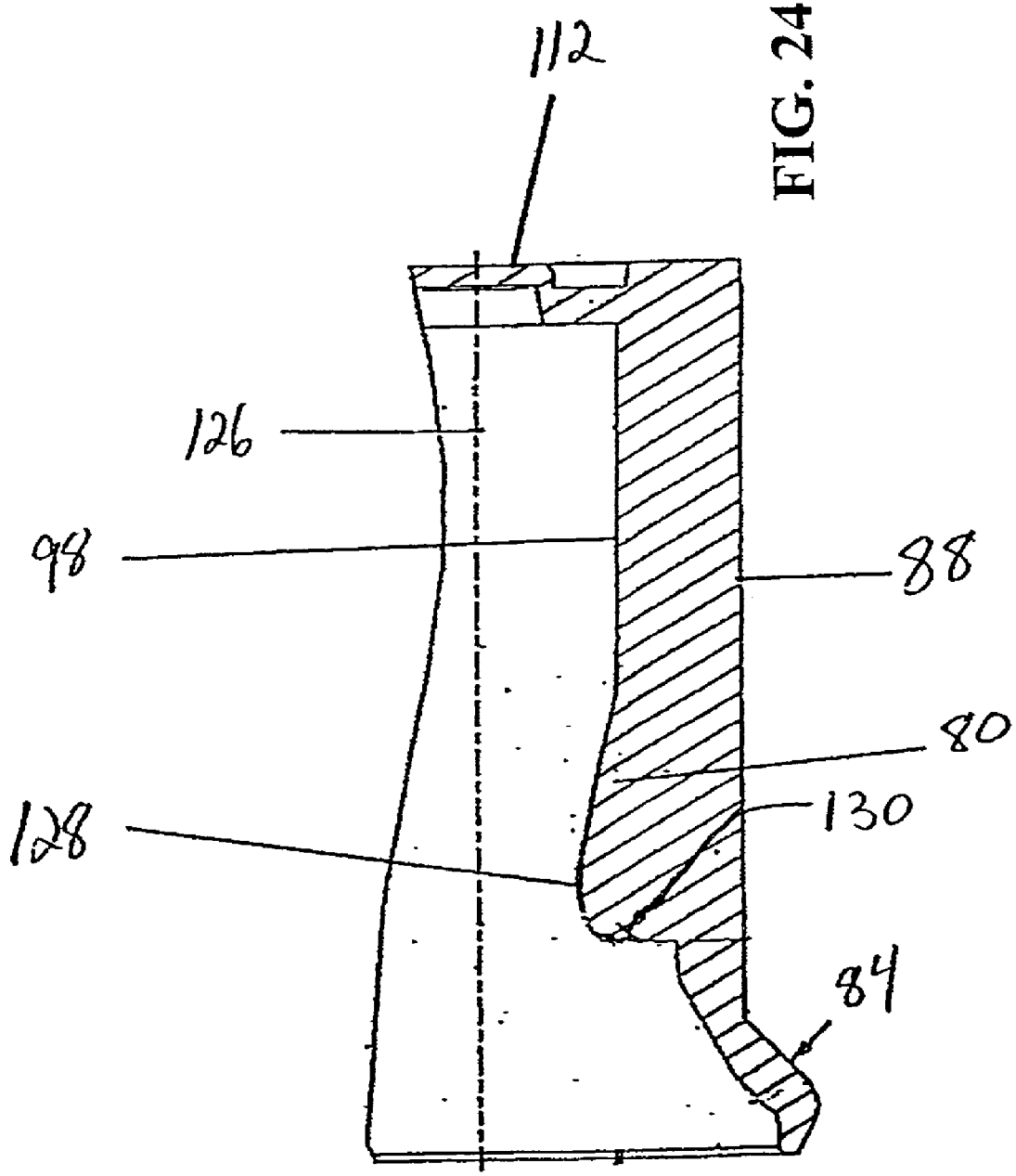
FIG. 24A is an exaggerated cut-away view showing a partial cross-section of an alternative embodiment of the impression cap.

Certain portions, which are indicated in FIG. 20, are blown up and can be seen in FIGS. 21, 22 and 24. FIG. 21 is a blow-up of section C in FIG. 20 and illustrates an alternative embodiment of the one way vent 112 at the top of the cap 110 in a cross-sectional view. The vent 112 comprises a cover 119, having fast first and second attachment pieces 121, 123, which attach the cover 119 to the top 125 of the cap 110. On either side of the cover 119, there is a vent opening 127, 129 in the form of slits to define air passages to release air when the cap is placed over the abutment piece. As with vent 90, the air passages close when impression material is pressed over the cap. Thus, the vent openings 127, 129, and thus slits are closeable. As with cap 32, a recess 93 may also be formed to keep the top surface of the cover 119 at, or below, surface 74.

FIG. 22 shows a cross-sectional view of the flange 44 portion of the cap 110, indicated as D in FIG. 20. The cross-section is through second vent 120. The portions numerically indicated are described above.

FIG. 23 shows a cross-sectional view of the flange 44 portion of the cap 110, indicated as J—J in FIG. 22. 110 indicates the cap material. The portions numerically indicated are described above.

FIG. 24 shows a cross-sectional view of a portion of the cap 110, indicated as F in FIG. 20. The cross-section is through abutment flat 80, perpendicular to the abutment surface 98. The portions numerically indicated are described above.

An additional individual feature may also be seen in this figure. In this embodiment, instead of the surface 98 of the abutment flat 80 being parallel with, or slightly angling away from, the center line 126, as shown in the other embodiments, a portion of the surface 98 angles toward the center line 126 forming a bulge 128. An exaggerated view of bulge 128 may be seen in FIG. 24a. The bulge 128 may be positioned at other places along the surface 98. In the embodiment shown, the bulge 128 is positioned on the lower part of the flat 80. Eventually, the surface 98 angles back away 130 from the center line 126. This bulge 128 or extension inward provides an alternative or additional press fit mechanism that provides an increase in rotational and vertical stability. The feature 128 also accounts for manufacturing tolerance by compressing the bulge 128 against the flat 80. It removes the necessity of having an exact fit between the internal geometry of the impression cap and the outer geometry of the abutment piece and the circumferential flange 44 and the collar 16 of the implant 10.

FIGS. 25 and 26 are views of the cap 110 from the top and bottom, respectively. The portions numerically indicated are described above.

FIG. 27 is a side view of cap 110 with rib 86 in the front. FIG. 28 is a cross-sectional view of a portion of FIG. 27, indicated as H—H. The portions numerically indicated are described above.

FIG. 29 is a view of the cap 110, wherein the vertical rib 88 is centered in the front. The lower portion of the cap 110 is cut away to reveal the channel 116. FIG. 30 is a cross-sectional view of a portion of FIG. 29, indicated as G—G. Rib 88 is shown as being wider than rib 86 so as to support the internal flat 80 geometry. It is also seen as shallower than rib 86 due to the indicator flat surface 78. The portions numerically indicated are described above.

Figure 31:
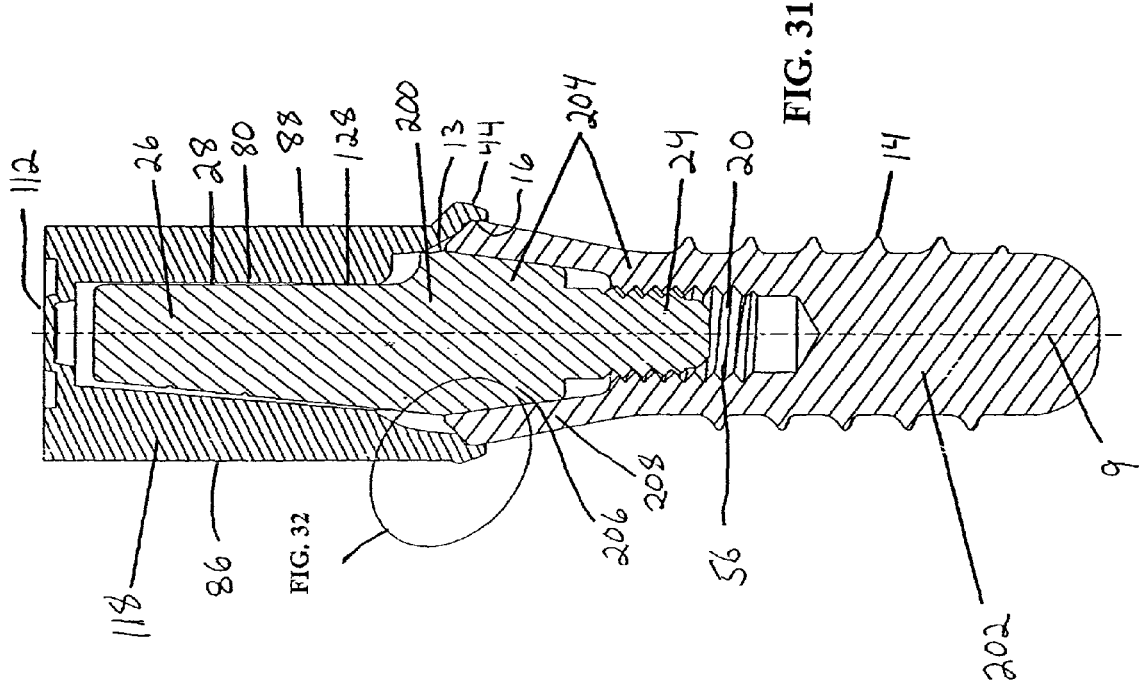
FIG. 31 is a cut-away view showing a partial cross-section of an implant/abutment assembly and an impression cap mounted thereon.

Similar to FIGS. 6–7, FIG. 31 illustrates a cross-sectional view of an embodiment of an impression cap 110 position on an abutment piece 200, which is in turn inserted in an implant 202. The device is positioned to view the abutment flat 28 from the side such that the cross section is through the first 13 and second 120 secondary vents. This particular embodiment incorporates the bulge 128 feature and uses cap 110, which may accommodate a situation where the internal geometry of the cap 110 is not an exact fit with the external geometry of the abutment piece, as shown.

In these figures, the impression cap 110 is positioned on an abutment 26 of an abutment piece 200, which is screwed into an implant 202 to illustrate the fit between the impression cap 110 and the abutment/implant assembly 204, as well as the fit between the abutment piece 200 and the implant 202. This particular embodiment illustrates a slightly different abutment/implant assembly 204. This particular embodiment utilizes a conical mating system for a secure and stable fit between the abutment piece 200 and the implant 202. This mating system differs from the system shown in FIGS. 6–7 in one respect in that it does not include the stepped feature 60, 62. The mating system shown in FIG. 31 utilizes a conical male portion 206 of the abutment piece 200 which fits into a conical female portion 208 of the implant 202.

Figure 32:
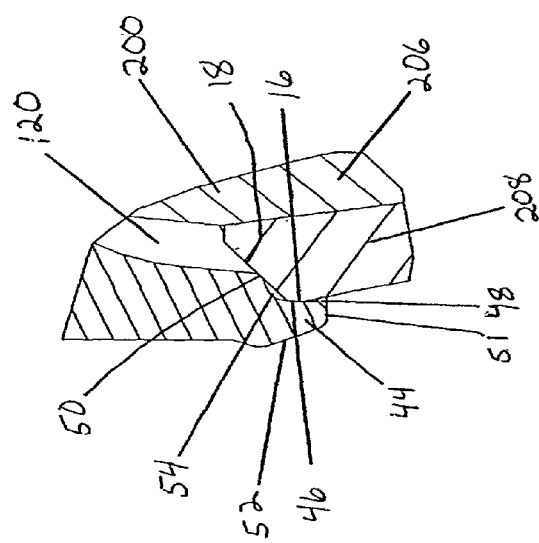
FIG. 32 is a detailed cut-away view showing a partial cross-section of a portion of FIG. 31, as indicated.

FIG. 32 is a blown-up view of a portion of FIG. 31, as indicated in FIG. 31. The cross-section portion is through the second secondary vent 120. The figure also illustrates the engagement between the press fit mechanism of the impression cap 110 and the implant 202. This engagement occurs primarily between the peripheral portions of the collar 16 of the implant 202 and the engagement end or press fit mechanism of the impression cap 110. As mentioned above, the press fit or friction fit of the impression cap is produced by the press fit mechanism of the cap. The mechanism provides an inwardly directed radial force against the periphery of the collar.

As shown in FIG. 32, at the engagement end, the press fit mechanism of the impression cap 110 has a circumferential flange 44 to guide the engagement end of the impression cap 110 over the collar 16 of the implant 202. The flange 44 has a press or squeeze surface 46 which is substantially parallel with the axis 9 of the implant 202 and press fits to the maximum diameter of implant collar 16. The connection between the flange 44 and the collar 16 is a pressure frictional fit, wherein the flange 44 squeezes the outer surface of the collar 16. The outer surface of the collar 16 which contacts the flange 44 may be flat to provide a greater contact surface.

The flange 44 further includes a lead in taper 48 to guide the flange 44 over the collar 16. During assembly of impression cap 110 onto implant 202, taper 48 contacts the outer surface of the implant collar 16 first. The taper 48 helps expand the impression cap 110 so that pressing surface 46 can press fit (or friction fit) to the maximum diameter of implant collar 16. The lead in taper 48 can be a chamfer, radius, or the like.

The flange 44 may have an extra surface 51 between angled surface 52 and surface 48 to provide a blunt end to the flange 44. Surface 51 may be substantially perpendicular to pressing surface 46 or rounded.

The impression cap 110 also comprises an angled surface 50 which provides a reference stop with the shoulder 18 of the implant 202, as described above. Surface 50 is only partially shown in these figures because the cross-section is through the secondary vents.

The flange 44 further includes angled surface 52 formed by its exterior. This surface 52 retracts the gingival tissue away from the implant table. This allows the impression cap 110 to automatically capture the implant margin, or collar 16. This also eliminates the need to pack cord, a common but tedious dental procedure.

As with the above described embodiment, the engagement end of the impression cap 110 also forms a curved relief 54 between angled surface 50 and the body of the flange 44. This relief 54 removes the acute angle formed between the pressing surface 46 and the angled or stop surface 50. The curved relief 54 removes any stress risers that may occur within the material during assembly as the lead in taper 48 moves over the implant collar.

FIGS. 31 and 32 further show the fit between the abutment piece 200 and the implant 202. The implant 202 has a bored hole 20, which is partially threaded 56 and partially conical 208. These portions receive threaded portion 24 and conical portion 206 of the abutment piece 200 for a secure fit.

The impression cap embodiments are made from any material compatible with dental usage and the impressing process. Suitably the material is an elastic or moldable material, including, but not limited to, thermoplastic materials, such as polypropylene, polyethylene, acetal (i.e., Delrin or Celcon), HDPE, PEEK, PEAK, or Thermoset. An elastic material is advantageous to provide sufficient squeezing force between the impression cap and the implant collar 16. The press/friction fit combined with the squeezing force provided by the elastic material provides sufficient retention of the impression cap to the implant.

It should be understood that individual features of the above embodiments may stand alone as improvement or may be combined with each other in multiple configurations where physically possible. The proportional representation illustrated by the figures also represents structural disclosure of various embodiments.

While press fitting the impression cap on the implant, the combination of the impression cap plastic material expanding during engagement of the implant outer collar diameter and the bottoming out of the impression cap on the implant table provides a tactile feel to the clinician that the impression cap is fully assembled to and self-centered on the implant.

The combination of the impression cap elastic material expanding during engagement of the implant outer collar diameter and the bottoming out of the impression cap on the implant table provides an audible sound to the clinician that the impression cap is fully assembled to and self-centered on the implant, while press fitting the impression cap on the implant.

The invention also contemplates sterilizing the impression cap via gamma sterilization. For this, a material must be chosen which is gamma sterilizable. Suitably a gamma sterilizable plastic, or more suitably a gamma sterilizable polypropylene, may be used.

The above described impression caps may be made by conventional means such as injection molding. Through injection molding, the caps may be a one piece structure.

The invention also contemplates color-coding the separate pieces to denote abutment length and table collar diameter. The impression cap color corresponds to the appropriate color coded abutment and abutment analog. This may be done to aid the physician in matching the appropriate pieces. This is helpful considering the small sized of the pieces. The colors may be imparted into the material being molded into the cap.

If not described in detail above, the proportions and relative construction of the embodiments may be interpreted from the figures. Any inconsistencies between the figures and the description should be seen as alternative embodiments. Variations in the relative construction which do not change the inventive concepts presented herein are contemplated as possible embodiments of the invention.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependet claim format which creates a dependency from a prior antecedent-possessing claim other than the specific claim listed in such dependent claim below (e.g. claim 6 may be taken as alternatively dependent from any of claims 2–5, claim 4 may be taken as alternatively dependent from claim 3; etc.).

What is claimed is:

1. A combination of an impression cap and a dental implant comprising:
    a dental implant having a longitudinal axis and a circumferential collar with an outermost diameter defining an outermost diameter portion; and
    an impression cap selectively connectable to and disconnectable from said dental implant for taking an impression, said impression cap comprising:
    an elongated body having a first end and a second end, at least the second end being provided with an opening, the opening extending longitudinally into the body from the second end forming an inner cavity;
    a press fit mechanism comprising a press fit surface formed near the second end of the body for squeezing against said outer circumferential collar of said dental implant to form a press fit connection between the dental implant and the impression cap, said press fit surface being an internal surface with an internal side wall in engagement with said outermost diameter portion of said circumferential collar when the impression cap and the dental implant are in said press fit connection, said internal side wall being substantially parallel to said longitudinal axis of the dental implant at the point of engagement between said internal side wall and said circumferential collar and said internal side wall extending in a direction substantially parallel to said longitudinal axis of the dental implant from said point of engagement toward said second end, wherein said impression cap is selectively connectable to said dental implant solely by said press fit connection.

2. The combination according to claim 1, wherein said circumferential collar includes an outer, upper shoulder and said impression cap includes an inner circumferential angled surface and having a size and shape complementary to said outer, upper shoulder.

3. The combination according to claim 2, the press fit mechanism comprising a circumferential flange extending downwardly toward said second end and from the body, the flange comprising said internal surface and said inner circumferential angled surface, said angled surface being mated to the upper shoulder of the implant when the impression cap and the dental implant are in said press fit connection.

4. The combination according to claim 3, the press fit mechanism further comprising a curved relief between the inner circumferential angled surface and the internal surface, said relief forming a gap between the impression cap and the implant when the impression cap is positioned on the implant.

5. The combination according to claim 3, the flange further comprising a tapered surface, said tapered surface extending downwardly from the internal surface and away from the implant.

6. The combination according to claim 3, the flange having a bottom end corresponding to said second end, the flange further comprising an outer angled surface, the outer angled surface extending downwardly and inwardly to the bottom end of the flange.

7. The combination according to claim 3, the body having an inner surface wall, said inner circumferential angled surface angling outwardly from the inner surface wall, wherein a channel is formed in the inner circumferential angled surface, such that a vent from the cavity to the outside is formed when the impression cap and the dental implant are in said press fit connection.

8. The combination according to claim 7, wherein there are at least two channels formed in the inner circumferential angled surface.

9. The combination according to claim 3 wherein the dental implant includes an implant table, the impression cap being elastic, wherein, while press fitting the impression cap on the implant, the combination of the impression cap elastic material expanding during engagement of the implant outer collar diameter and the bottoming out of the impression cap on the implant table provides a tactile feel to a clinician that the impression cap is fully assembled to and self-centered on the implant.

10. The combination according to claim 3, wherein the impression cap is color coded to denote abutment length and implant collar diameter and correspond to the appropriate color coded abutment and abutment analog.

11. The combination according to claim 1, the impression cap having a one-way vent positioned at the first end of the cap.

12. The combination according to claim 1, wherein the body comprises: a side wall having an outer surface; and at least one circumferential rib protruding outward from the outer surface of the side wall.

13. The combination according to claim 12, the body comprising two circumferential ribs protruding outward from the outer surface of the side wall, wherein the two circumferential ribs are spaced apart along the longitudinal axis of the body.

14. The combination according to claim 13, at least one of the circumferential ribs having a flat surface which serves as an external abutment feature during an impression procedure enabling proper positioning of an abutment analog to reproduce a abutment orientation and implant position.

15. The combination according to claim 13, wherein the circumferential ribs comprise at least one concave surface around their periphery.

16. The combination according to claim 12, further comprising a first vertical rib protruding outward from the outer surface of the side wall and extending from the first end of the body to the second end.

17. The combination according to claim 16, further comprising a second vertical rib, wherein the vertical ribs are spaced 180 degrees apart from one another around the periphery of the cap.

18. The combination of claim 1 wherein a portion of said internal side wall extends past said outermost diameter portion when the impression cap and the dental implant are in said press fit connection.

19. The combination of claim 1 wherein said dental implant includes an abutment.

20. The combination of claim 19 wherein said abutment extends into said internal cavity when the impression cap and the dental implant are in said press fit connection.

21. The combination of claim 20 wherein said abutment is selectively connectable to said dental implant.

22. The combination of an impression cap and a dental implant comprising:
   a dental implant having an outer circumferential collar; and
   an impression cap comprising:
   an elongated body having a longitudinal axis, a first end and a second end, at least the second end being provided with an opening, the opening extending longitudinally into the body from the second end forming an inner cavity, the body further comprising a side wall having an outer surface and two circumferential ribs protruding outward from the outer surface of the side wall, wherein the two circumferential ribs are spaced apart along the longitudinal axis of the cap and wherein at least one of the circumferential ribs has a flat surface which serves as an external abutment feature during an impression procedure enabling proper positioning of an abutment analog to reproduce an abutment orientation and implant position;
   a press fit mechanism formed in the second end of the body, for squeezing against said outer circumferential collar of said dental implant, said circumferential collar having an outer diameter and said dental implant having a longitudinal axis, a top and a bottom, wherein the press fit mechanism squeezes against the collar of the dental implant via a press fit, such that, when the press fit mechanism squeezes against the collar, the portions of the press fit mechanism which are at or below the outer diameter of the collar have an inner diameter which is equal to or greater than the outer diameter of the collar; and
   a first vertical rib protruding outward from the outer surface of the side wall and extending from the first end of the body to the second end.

23. The combination according to claim 22, further comprising a second vertical rib, the first vertical rib being aligned with the flat surface on the at least one circumferential rib.

24. The combination of an impression cap and a dental implant comprising:
   a dental implant having an outer circumferential collar; and
   an impression cap comprising:
   an elongated body having a longitudinal axis, a first end and a second end, at least the second end being provided with an opening, the opening extending longitudinally into the body from the second end forming an inner cavity, the body further comprising a side wall having an outer surface; and at least one circumferential rib protruding outward from the outer surface of the side wall;
   a press fit mechanism formed in the second end of the body, for squeezing against said outer circumferential collar of said dental implant, said circumferential collar having an outer diameter and said dental implant having a longitudinal axis, a top and a bottom, wherein the press fit mechanism squeezes against the collar of the dental implant via a press fit, such that, when the press fit mechanism squeezes against the collar, the portions of the press fit mechanism which are at or below the outer diameter of the collar have an inner diameter which is equal to or greater than the outer diameter of the collar;
a first vertical rib protruding outward from the outer surface of the side wall and extending from the first end of the cap to the second end and a second vertical rib, wherein the first and second vertical ribs are spaced 180 degrees apart from one another around the periphery of the cap; and
an inner cavity, wherein the inner cavity of the impression cap has an inner geometry which comprises an internal abutment flat and has a size and shape complementary to an abutment piece which may be secured in the implant, the first vertical rib being aligned with the internal abutment flat, the first and second vertical ribs having a width and a depth, wherein the width of the first vertical rib is greater than the width of the second vertical rib substantially along their lengths.

25. The combination according to claim 24, wherein the second vertical rib extends from the first end of said body to the second end and thickens at the second end.

26. The combination according to claim 24, wherein the internal abutment flat comprises an abutment surface facing inward, the abutment surface comprising a bulge extending inward.

27. A combination of an impression cap and a dental implant comprising:
a dental implant having an outer circumferential collar; and
an impression cap comprising:
an elongated, generally conical body having a longitudinal axis, a first end and a second end, at least the second end being provided with an opening, the opening extending longitudinally into the body from the second end forming a inner cavity wherein the inner cavity of the impression cap has an inner geometry which comprises an internal abutment flat and has a size and shape complementary to an abutment piece which may be secured in the implant and wherein the internal abutment flat comprises an abutment surface facing inward, the abutment surface comprising a bulge extending inward; and
a press fit mechanism formed in the second end of the body, for squeezing against said outer circumferential collar of said dental implant, said circumferential collar having an outer diameter and said dental implant having a longitudinal axis, a top and a bottom, wherein the press fit mechanism squeezes against the collar of the dental implant via a press fit, such that, when the press fit mechanism squeezes against the collar, the portions of the press fit mechanism which are at or below the outer diameter of the collar have an inner diameter which is equal to or greater than the outer diameter of the collar.

28. An impression cap comprising:
a cylinder shaped body having a longitudinal axis, a first end and a second end wherein said first end is substantially closed forming a top and at least the second end being provided with an opening to engage an abutment piece, the opening extending longitudinally into the body from the second end forming an inner cavity, the cylinder shaped body further having an inner surface and an outer surface, the impression cap further comprising a first groove formed in the inner surface adjacent the second end, such that, when the impression cap is placed over the abutment piece, air is vented between the first groove and the abutment piece; and
a one-way vent formed in said top.

29. An impression cap according to claim 28, further comprising a second groove formed in the inner surface adjacent the second end, such that, when the impression cap is placed over the abutment piece, air is vented between the second groove and the abutment piece.

30. An impression cap according to claim 29, wherein the first and second grooves are positioned in the inner surface in opposing fashion.

31. An impression cap according to claim 28, further comprising a press fit mechanism formed in the second end of the body, for squeezing an outer circumferential collar of a dental implant, said circumferential collar having an outer diameter and said dental implant having a longitudinal axis, a top and a bottom, wherein the press fit mechanism squeezes the collar of the dental implant via a press fit, such that, when the press fit mechanism squeezes the collar, the portions of the press fit mechanism which are at or below the outer diameter of the collar have an inner diameter which equal to or greater than the outer diameter of the collar.

32. An impression cap according to claim 28, wherein the cylinder-shaped body has a generally conical inner cavity.

33. An impression cap for a dental impression system, comprising:
an elongated body having a longitudinal axis, a first end and a second end, at least the second end being provided with an opening to engage an abutment piece, the opening extending longitudinally into the body from the second end forming an inner cavity, the elongated body further having an inner surface and an outer surface, the impression further comprising a first groove formed in the inner surface adjacent the second end, such that, when the impression cap is placed over the abutment piece, air is vented between the first groove and the abutment piece and a second groove formed in the inner surface adjacent the second end, such that, when the impression cap is placed over the abutment piece, air is vented between the second groove and the abutment piece, the impression cap further comprising a first vertical rib protruding outward from the outer surface of the side wall and extending from the first end of said body to the second end and a second vertical rib, wherein the vertical ribs are spaced apart circumferentially from one another around said body, wherein the inner cavity of the impression cap has an inner geometry which comprises an internal abutment flat and has a size and shape complementary to the abutment piece, the first vertical rib being aligned with the internal abutment flat, the vertical ribs having a width and a depth, wherein the width of the first vertical rib is greater than the width of the second vertical rib substantially along their lengths.

34. An impression cap according to claim 33, wherein the two vertical ribs are aligned with the grooves.

35. An impression cap for a dental impression system, comprising:
an elongated body having a longitudinal axis, a first end and a second end at least the second end being provided with an opening to engage an abutment piece, the opening extending longitudinally into the body from the second end forming an inner cavity, the elongated body further having an inner surface and an outer surface, the impression cap further comprising an abutment flat formed in the inner surface and a bulge formed on the abutment flat which extends inward to create a press fit when the cap is placed over an abutment piece, the impression cap further comprising a first groove formed in the inner surface adjacent the second end, such that, when the impression cap is placed over the abutment piece, air is vented between the first groove and the abutment piece.

36. An impression cap according to claim 35, wherein said first end is substantially closed forming a top.

37. An impression cap according to claim 35, further comprising a press fit mechanism formed in the second end of the body, for squeezing an outer circumferential collar of a dental implant, said circumferential collar having an outer diameter and said dental implant having a longitudinal axis, a top and a bottom, wherein the press fit mechanism squeezes the collar of the dental implant via a press fit, such that, when the press fit mechanism squeezes the collar, the portions of the press fit mechanism which are at or below the outer diameter of the collar have an inner diameter which equal to or greater than the outer diameter of the collar.

38. An impression cap for a dental impression system, comprising:

an elongated body having a longitudinal axis, a first end and a second end, the first end of the body being substantially closed forming a top and at least the second end being provided with an opening to engage an abutment piece, the opening extending longitudinally into the body from the second end forming an inner cavity, the elongated body further having an inner surface and an outer surface, the impression cap further comprising an abutment flat formed in the inner surface, a bulge formed on the abutment flat which extends inward to create a press fit when the body is placed over an abutment piece and a one-way vent formed in the top of the body.

39. An impression cap for a dental impression system, comprising:

a cylinder shaped body having a longitudinal axis, a first end and a second end, at least the second end being provided with an opening, the opening extending longitudinally into the body from the second end forming an inner cavity, the cylinder shaped body further having an inner surface and an outer surface, the impression cap further comprising an abutment flat formed in the inner surface and an external geometry formed on the outer surface, the body comprising two circumferential ribs protruding outward from the outer surface of the side wall, wherein the two circumferential ribs are spaced apart along said longitudinal axis, the impression cap further comprising a first vertical rib protruding outward from the outer surface of the side wall and extending from said first end to the second end.

40. An impression cap according to claim 39, further comprising a second vertical rib, wherein the vertical ribs are spaced apart from one another around the periphery of the cap.

41. An impression cap according to claim 40, the first vertical rib being aligned with the internal abutment flat, the vertical ribs having a width and a depth, wherein the width of the first vertical rib is greater than the width of the second vertical rib substantially along their lengths.

* * * * *